(12) United States Patent
Colesanti et al.

(10) Patent No.: US 8,690,889 B2
(45) Date of Patent: Apr. 8, 2014

(54) METHOD AND APPARATUS FOR SURGICAL FASTENING

(75) Inventors: Anthony Colesanti, Bristol, RI (US); Augustus Felix, Cranston, RI (US); Alan Bachman, Milford, CT (US); Ray Adams, Ansonia, CT (US); Joseph Paul, Thomaston, CT (US); Jeff Stein, Woodbridge, CT (US)

(73) Assignee: Davol, Inc., Warwick, RI (US)

( * ) Notice: Subject to any disclaimer, the term of this patent is extended or adjusted under 35 U.S.C. 154(b) by 456 days.

(21) Appl. No.: 12/761,732

(22) Filed: Apr. 16, 2010

(65) Prior Publication Data

US 2011/0071578 A1    Mar. 24, 2011

Related U.S. Application Data

(63) Continuation of application No. 12/550,618, filed on Aug. 31, 2009, now abandoned, which is a continuation of application No. 12/354,147, filed on Jan. 15, 2009, now abandoned, which is a continuation of application No. PCT/US2007/015952, filed on Jul. 13, 2007.

(60) Provisional application No. 60/831,712, filed on Jul. 18, 2006.

(51) Int. Cl.
| | | |
|---|---|---|
| *A61B 17/58* | (2006.01) |
| *A61B 17/60* | (2006.01) |
| *A61F 5/04* | (2006.01) |
| *A61B 17/04* | (2006.01) |
| *A61B 17/86* | (2006.01) |
| *A61F 2/08* | (2006.01) |
| *A61B 17/84* | (2006.01) |

(52) U.S. Cl.
USPC .............. 606/104; 606/99; 606/304; 606/329

(58) Field of Classification Search
USPC ............ 606/104, 99, 304, 329; 206/338, 343, 206/820
See application file for complete search history.

(56) References Cited

U.S. PATENT DOCUMENTS

| | | | |
|---|---|---|---|
| 5,730,744 A | | 3/1998 | Justin et al. |
| 5,735,854 A | * | 4/1998 | Caron et al. .................. 606/916 |
| 2004/0204723 A1 | | 10/2004 | Kayan |
| 2005/0149031 A1 | * | 7/2005 | Ciccone et al. .................. 606/73 |
| 2005/0171562 A1 | * | 8/2005 | Criscuolo et al. ............. 606/151 |

FOREIGN PATENT DOCUMENTS

FR    2 879 915 A    6/2006

* cited by examiner

*Primary Examiner* — David Bates
(74) *Attorney, Agent, or Firm* — Wolf, Greenfield & Sacks, P.C.

(57) ABSTRACT

A surgical fastener system includes a plurality of fasteners having a throughbore with a non-circular cross section portion. The fasteners may engage with a splined mandrel that passes through the throughbore of the fasteners and rotates the fasteners relative to the mandrel to move at least one of the fasteners along the mandrel, e.g., along the mandrel's longitudinal axis. A distal end of the mandrel may be inserted into a material, such as a tissue, prosthetic or other, and a fastener may be deployed from the distal end of the mandrel while the distal end is positioned in the material.

26 Claims, 7 Drawing Sheets

METHOD AND APPARATUS FOR SURGICAL FASTENING

This application is a continuation of U.S. application Ser. No. 12/550,618, filed Aug. 31, 2009 which is a continuation of U.S. application Ser. No. 12/354,147, filed Jan. 15, 2009 which is a continuation of PCT/US2007/015952, filed Jul. 13, 2007 and claims the benefit of U.S. provisional application No. 60/831,712, filed Jul. 18, 2006.

BACKGROUND

1. Field of Invention

This invention relates to methods and apparatus for surgical fastening.

2. Related Art

Surgical fasteners are widely used in many different medical procedures. For example, staples, sutures, clips and other fasteners are commonly used in laparoscopic and open surgical procedures to secure two or more portions of tissue, prosthetic, or other material relative to each other. The fasteners may provide a permanent connection between two portions, such as between bone and a non-absorbable prosthetic, or may provide a more temporary fixation, such as between a mesh prosthetic and muscle or other tissue to allow tissue ingrowth or other healing processes to more securely fixate the mesh relative to the tissue.

For example, U.S. Patent Publication 2004/0049227 to Jervis discloses a helical fastener and applicator for attaching a prosthesis to tissue, e.g., to attach a mesh prosthetic in a hernia repair procedure. The applicator disclosed in Jervis may deploy one or more fasteners having a helical wire coil shape by using a rotator to rotate and discharge the fasteners from a distal end of the applicator. In one embodiment, a stationary stabilizer rod located at an inner portion of the coil fasteners has a thread form that engages with the fasteners and feeds the fasteners distally as they are rotated.

Other fasteners used to secure mesh in a surgical procedure, such as hernia repair, are disclosed in U.S. Patent Publication 2004/0204723 to Kayan and U.S. Patent Publication No. 2005/0171562 to Criscuolo, among others. In both Kayan and Criscuolo, the fasteners include a thread form and head on a screw-like structure. These fasteners are also said to be made of an absorbable material. Thus, the fasteners may degrade and be absorbed by the body after the surgical procedure is complete.

SUMMARY OF THE INVENTION

In one aspect of the invention, a surgical fastener includes a barrel portion with a helical thread extending from near a distal end of the barrel portion toward a proximal end of the barrel portion. A head portion may be located at the proximal end of the barrel portion, and a throughbore may extend through the head portion and the barrel portion. The throughbore may include a splined portion, and the barrel portion and the head portion may be formed of a bioabsorbable material. In one embodiment, the throughbore may have an unsplined portion located at a proximal end of the throughbore. The splined portion may be located at a distal end of the throughbore, and the unsplined portion may extend over approximately half a length of the throughbore. The head portion of the fastener may include at least one alignment feature adapted to allow a plurality of fasteners to be aligned together on a mandrel. For example, the at least one alignment feature may include a flat portion on one side of the head portion.

In another aspect of the invention, a surgical fastener includes a barrel portion with a longitudinal axis and a helical thread extending from near a distal end of the barrel portion toward a proximal end of the barrel portion. A head portion may be attached at the proximal end of the barrel portion. A throughbore may extend along the longitudinal axis through the head portion and the barrel portion, and the barrel portion and head portion may be formed of a bioabsorbable material. In one embodiment, the distal end of the barrel portion may have a crenellated tip feature. The crenellated tip may help the distal end of the fastener penetrate a material, such as a mesh material and/or may help lead the fastener into a material by allowing the distal end of the fastener to closely conform to the shape of a mandrel on which the fastener is mounted.

In another aspect of the invention, a surgical fastener system includes a tube having a distal end, a proximal end, and an inner bore with an internal threaded portion. A plurality of fasteners may be located in the tube, with each of the fasteners having a barrel portion with an external thread and a throughbore extending through the barrel portion. The throughbore may have a portion with a non-circular cross-section that receives and engages with a mandrel also located in the inner bore. The mandrel may have a distal end, and a longitudinal axis and be arranged for rotation about the longitudinal axis. A pusher element may be adapted to engage with the mandrel for rotation with the mandrel and engage with the internal threaded portion of the inner bore. Thus, rotation of the mandrel about the longitudinal axis may cause rotation of at least one of the fasteners engaged with the mandrel as well as rotation of the pusher element relative to the internal threaded portion. Rotation of the pusher element may cause the pusher element to move along the direction of the longitudinal axis in the inner bore, e.g., to urge fasteners on the mandrel to move distally. In one embodiment, the mandrel has a cruciform shape in a cross-section perpendicular to the longitudinal axis, and the non-circular cross section for each of the fasteners is a cruciform shape complementary to the cruciform shape cross section of the mandrel.

In another aspect of the invention, a surgical fastener system includes a tube having a distal end, a proximal end, and an inner bore. A plurality of fasteners may be located in the tube, with each of the fasteners having a barrel portion with an external thread and a throughbore extending through the barrel portion. The throughbore may have a portion with a non-circular cross-section, and a mandrel also located in the inner bore may pass through and engage with the throughbore of the plurality of fasteners. The mandrel may have a distal end, and a longitudinal axis and be arranged for rotation about the longitudinal axis. Rotation of the mandrel about the longitudinal axis may cause rotation of at least one of the fasteners engaged with the mandrel and deployment of the at least one fastener from the distal end of the tube. None of the fasteners proximal of the distalmost fastener may engage with the inner bore of the outer tube so as to resist axial or rotational movement of the fasteners relative to the tube.

In another aspect of the invention, a surgical fastener system includes a tube having a distal end, a proximal end, and an inner bore. A plurality of fasteners may be located in the tube, with each of the fasteners having a barrel portion with an external thread and a throughbore extending through the barrel portion. The throughbore may have a portion with a non-circular cross-section. A mandrel may be located in the inner bore and adapted to pass through the throughbore of the plurality of fasteners and engage with the non-circular cross-sectional portion of at least one of the plurality of fasteners. The mandrel may have a distal end, and a longitudinal axis and be arranged for rotation about the longitudinal axis and movement along the longitudinal axis relative to the tube. Rotation of the mandrel about the longitudinal axis may cause rotation of at least one of the fasteners engaged with the mandrel and deployment of the at least one fastener from the distal end of the tube.

These and other aspects of the invention will be apparent from the following description and claims.

BRIEF DESCRIPTION OF THE DRAWINGS

Aspects of the invention are described below with reference to illustrative embodiments, wherein like numerals reference like elements, and wherein.

DETAILED DESCRIPTION

It should be understood that aspects of the invention are described herein with reference to the figures, which show illustrative embodiments in accordance with aspects of the invention. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention.

In one aspect of the invention, a fastener applying system may include a plurality of fasteners that each include a barrel portion with an external thread and a throughbore extending through the barrel portion, e.g., along the barrel's longitudinal axis. The fasteners may each include a head portion that may be wider than the barrel portion and/or the external thread on the barrel. The fasteners may be arranged along a mandrel that has a splined portion and extends through the throughbore of the fasteners. At least a part of the throughbore of each fastener may have an internally splined portion that engages with the splined portion of the mandrel. The mandrel may rotate about its longitudinal axis so as to cause the fasteners to rotate. A pusher element at a proximal end of the fasteners may also engage with the mandrel and engage with an internal threaded portion of a tube that houses the fasteners. Thus, as the mandrel, fasteners and pusher element rotate relative to the tube, the pusher element may be driven to move distally on the mandrel, pushing the fasteners to move distally as well.

The fastener system may be used to deploy the fasteners in a subject tissue or other material, e.g., to secure a mesh to a muscle tissue in a hernia repair procedure. To deploy a fastener, a leading or distal end of the mandrel may first be positioned adjacent a subject material. In one illustrative embodiment, the mandrel may be inserted into the subject material, e.g., a pointed end of the mandrel may be inserted into the subject material. The mandrel may rotate at least a fastener located nearest the distal end of the mandrel so as to advance the fastener into the subject material. The distalmost and other fasteners on the mandrel may be fed toward the distal end of the mandrel, e.g., by a pusher element that rotates with the mandrel and engages a threaded portion in an outer tube so that the pusher element is forced distally on the mandrel. As the distalmost fastener is rotated, the external thread on the fastener barrel may engage with the subject material (e.g., mesh, tissue and/or other) and draw the fastener into the material. A head provided on the fastener may aid in seating the fastener at the material surface, aid in holding two or more materials together, and/or prevent over-inserting the fastener into the material.

Figure 1:
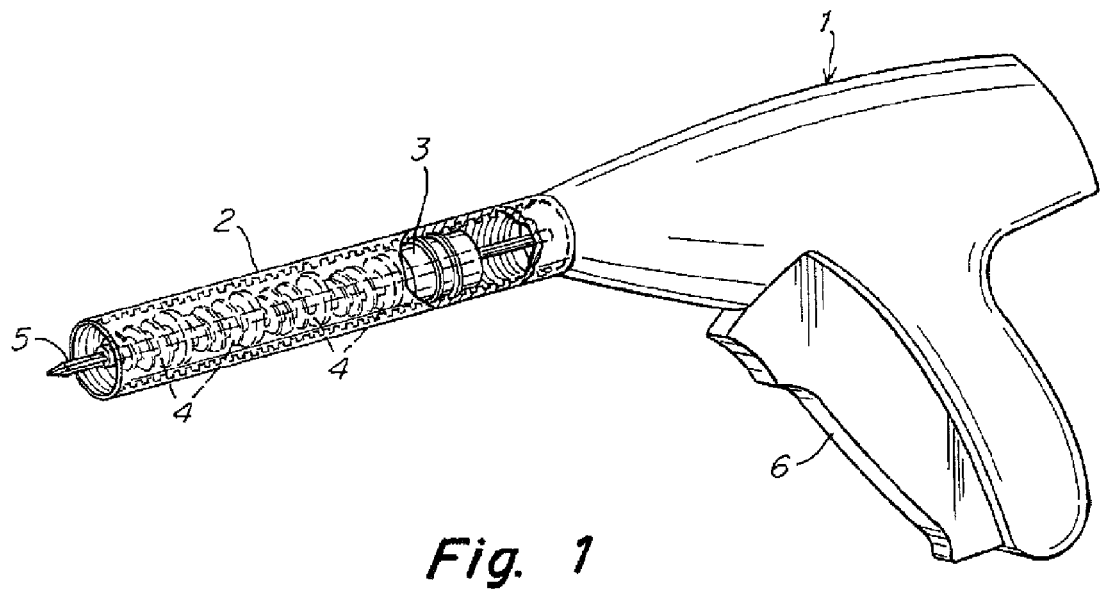
FIG. 1 is a perspective view of a fastener applier in accordance with aspects of the invention.
Figure 2:
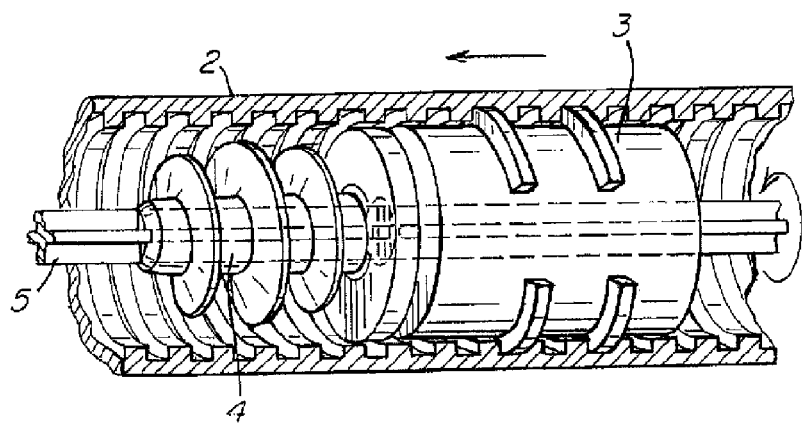
FIG. 2 shows a partial cross section of the shaft of the applier of FIG. 1.

FIG. 1 shows a fastener applier 100 and associated fasteners in an illustrative embodiment. The applier 100 includes a handle 1 and a shaft 2 extending distally from the handle 1. The shaft 2 houses a plurality of fasteners 4 on a mandrel 5 that are arranged so that the fasteners 4 rotate with the mandrel 5 when the mandrel 5 rotates about its longitudinal axis, but are otherwise generally free to move axially along the mandrel 5. A pusher element 3 at a proximal end of the fasteners 4 is arranged like the fasteners 4 to rotate with the mandrel 5, and is movable axially along the mandrel 5. As shown in the partial cross section of FIG. 2, the pusher element 3 also engages with an internally threaded portion of the shaft 2 so that as the pusher element 3 rotates with the mandrel 5, the pusher element 3 moves distally along the mandrel 5, pushing the fasteners 4 distally. The pusher element 3 may take any suitable form, and in this embodiment includes a cylindrical plug with thread elements that engage with the internal threads on the shaft 2. In addition, the pusher element 3 need not be rotated by the mandrel 5, but instead may be rotated by a separate drive element. In other embodiments, the pusher element 3 need not rotate, and instead may urge fasteners 4 to move distally in other ways, such as by a spring, a tape drive, or other arrangement. A trigger or other actuator 6 on the handle 1 may be operated by a user to rotate the mandrel 5, and to move the mandrel 5 distally relative to the shaft 2, e.g., so that a pointed end on the mandrel 5 is exposed from the distal end of the shaft 2. Once the distalmost fastener 4 is deployed, the mandrel 5 may retract within the shaft 2.

Figure 3:
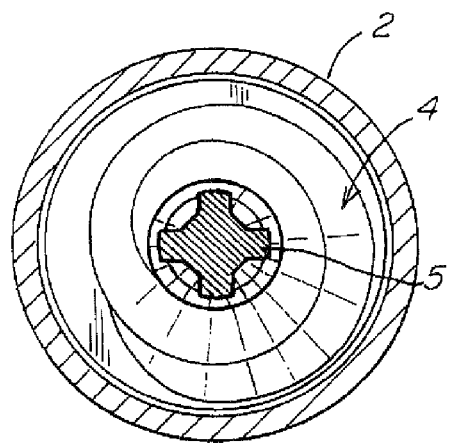
FIG. 3 is an end view of the distal end of the applier of FIG. 1.
Figure 4:
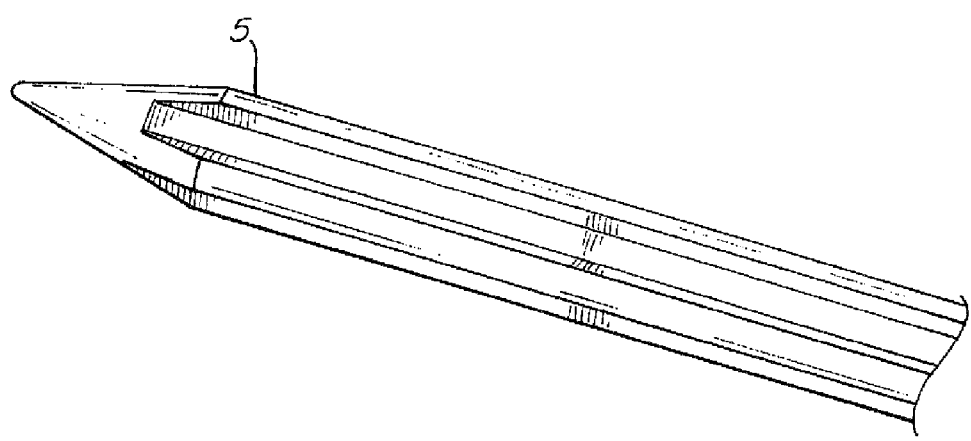
FIG. 4 shows a perspective view of the distal end of the mandrel.

As can be seen in FIG. 3, in this embodiment the shaft 2 has a tubular shape with an approximately circular cross section. The inside surface of the shaft 2 may (or may not) engage with the fasteners 4, e.g., to help align the fasteners 4 and prevent wobbling of the mandrel 5 during rotation, and allow the fasteners 4 to move axially along the mandrel 5. As can be seen in FIGS. 3 and 4, the mandrel 5 in this embodiment has a cruciform-shaped cross section, i.e., having four longitudinal splines arranged symmetrically around the mandrel 5. However, the mandrel 5 in some embodiments may have other cross sectional shapes, such as hexagonal, square, star-shaped or other cross section so as to engage with corresponding surfaces on the fasteners 4. In other embodiments, the mandrel 5 may have two or more longitudinally extending portions that engage with fasteners 4, such as a pair of prongs that extend longitudinally through the shaft 2 and through corresponding holes or grooves in the fasteners 4. Also, although in this embodiment all of the fasteners on the mandrel 5 are rotated with the mandrel, in other arrangements, the mandrel 5 may only rotate the distalmost fastener 4, and trailing fasteners may not rotate. For example, the mandrel 5 may only include a splined portion near a distal end of the shaft, and more proximal portions of the mandrel 5 may have a smooth cylindrical surface or other arrangement that does not engage with fasteners 4 so as to cause rotation of the fasteners.

Figure 5:
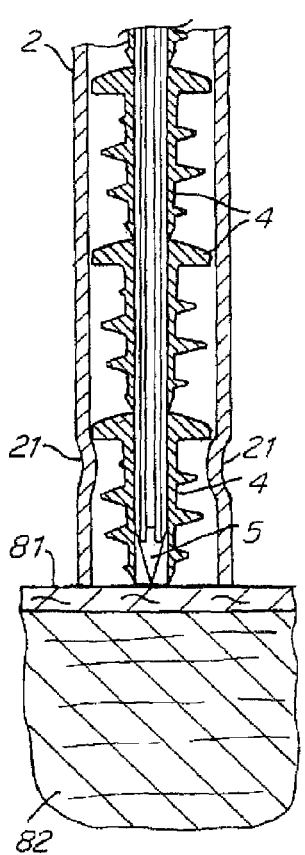
FIGS. 5-7 show a cross-sectional view of the distal end of the applier in various stages of deploying a fastener.
Figure 6:
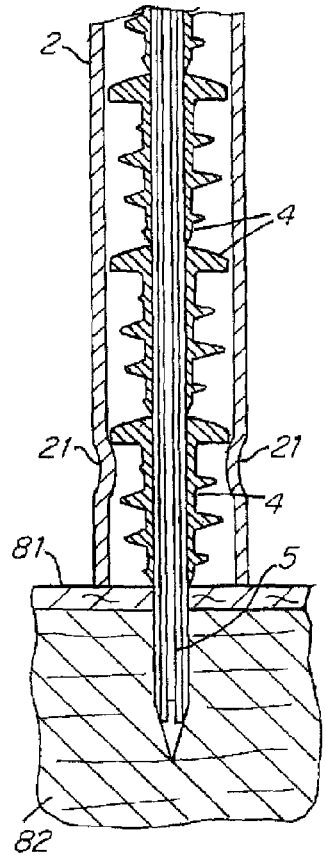
Figure 7:
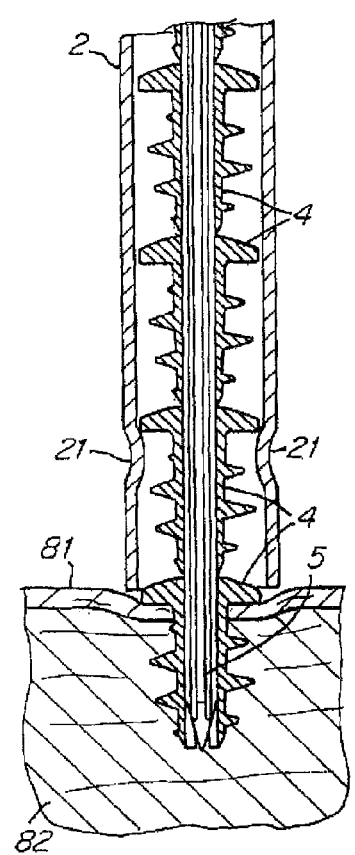

FIGS. 5-7 show a fastener being deployed by the applier 100 in FIG. 1. In FIG. 5, a user may position the distal end of the shaft 2 against a subject material, such as a mesh prosthetic 81 positioned on a muscle tissue 82. At this point, the mandrel 5 and the distalmost fastener 4 may be located within the shaft 2 (although in other embodiments, the mandrel 5 and/or the fastener 4 may be exposed). Actuation of the applier 100 may initially extend the mandrel 5 outside of the distal end of the shaft 2 so that the mandrel 5 penetrates the mesh 81 and/or tissue 82. In this embodiment, the mandrel 5 has a sharpened tip to aid in puncturing the subject material, but other arrangements are possible, such as a gimlet feature, a conical tip, blunt end or other on the mandrel's distal end. Alternately, the mandrel 5 may not penetrate the subject material, but rather may only press against the material or be positioned adjacent the material, e.g., in embodiments in which the mandrel 5 does not extend distally from the shaft 2. Also in this embodiment, the mandrel 5 extends into the subject material without rotation, but in some embodiments, the mandrel 5 may rotate as it punctures the subject material, e.g., to aid in entry into the material. During distal extension of the mandrel 5, the pusher element 3 and fasteners 4 may remain stationary. The distalmost fastener 4 may be held in place by a restriction element 21 of the shaft 2. The restriction element 21 may include a narrowed diameter portion of the shaft 2, one or more bumps, fingers, spring loaded elements or other features to help retain the fasteners 4 in the shaft 2 as the mandrel 5 is extended. (It should be understood that exposure of the mandrel 5 from the distal end of the shaft 2 may occur by having the distal end of the shaft 2 retract proximally, e.g., as the shaft's distal end is pressed against the material, in addition to, or instead of, having the mandrel 5 move distally.)

With the mandrel 5 extended into the material as shown in FIG. 6, the mandrel 5 may be rotated about its longitudinal axis. This causes the pusher element 3 and fasteners 4 to rotate with the mandrel 5 and move distally as the pusher element 3 moves distally. As the distal tip of the distalmost fastener 4 emerges from the shaft 2, the fastener 4 penetrates the mesh 81 and the tissue 82. In addition to the force of the pusher element 3 pushing on the stack of fasteners 4 on the mandrel to urge the distalmost fastener 4 past the restriction element 21, the external thread on the fastener 4 may engage with the mesh 81 and tissue 82 and help to pull the fastener into the material. With suitable rotation of the fastener 4, the fastener 4 is fully inserted into the material as shown in FIG. 7. The fastener 4 may then be disengaged from the mandrel 5, as the mandrel 5 and/or shaft 2 are pulled away from the fastener to deploy the fastener 4 from the applier 100. The mandrel 5 may be retracted into the shaft 2 to the position shown in FIG. 5, ready to deploy a next fastener in the applier 100. Note that the next distalmost fastener 4 is maintained in the shaft by the restriction element 21, e.g., so the fastener 4 is not dropped from the shaft 2 until forced out by the pusher element 3.

Figure 8:
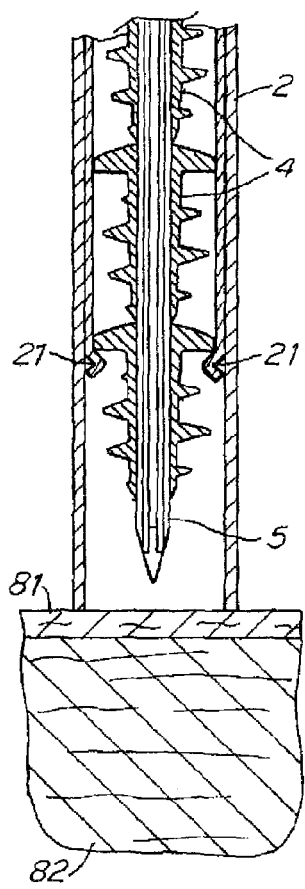
FIGS. 8-10 show a cross-sectional view of the distal end of an applier of an alternate embodiment in various stages of deploying a fastener.
Figure 9:
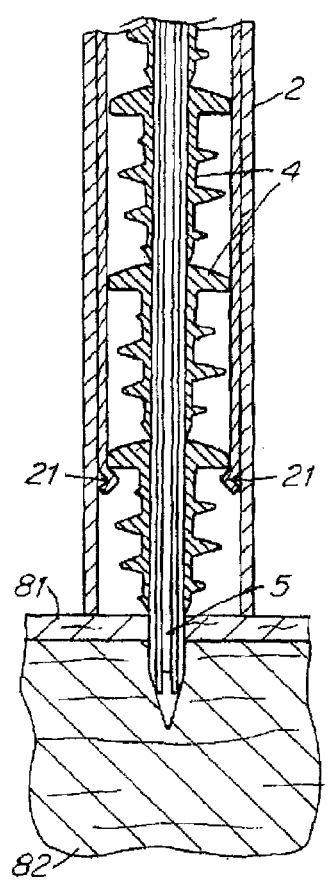
Figure 10:
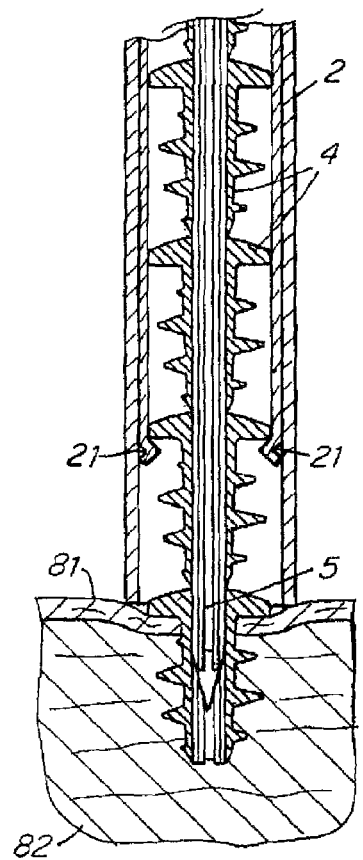

FIGS. 8-10 show another illustrative embodiment of an applier 100 that uses a different restriction element 21 than the above embodiment. In this embodiment, the restriction element 21 includes an inner tube that has spring fingers, a swaged portion or other restriction feature. The inner tube may or may not be movable in the shaft 2.

Figure 11:
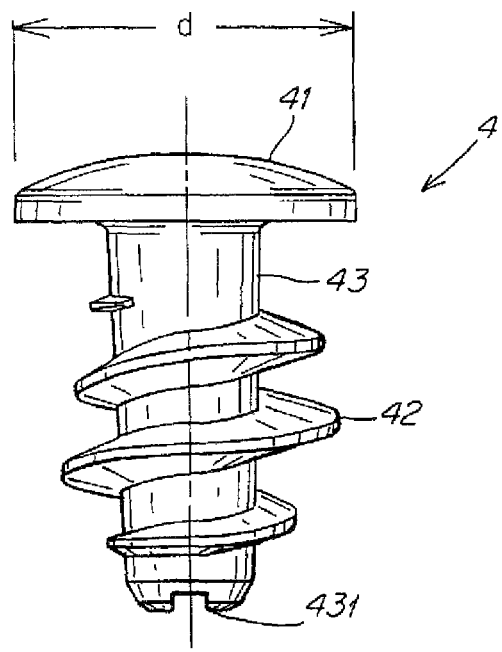
FIG. 11 shows a side view of a fastener in accordance with aspects of the invention.

Fasteners 4 used with the applier 100 may have any suitable arrangement, as will be appreciated by those of skill in the art. FIGS. 11-14 show various views of a fastener 4 in an illustrative embodiment. FIG. 11 shows a side view of the fastener 4, which has a head 41, an external helical thread 42 and a barrel portion 43. The head 41 may have any suitable shape and/or size, and in this embodiment has a generally flat distal face near the thread 42 and a rounded proximal face. The external thread 42 may have a diameter d that is close in size to the head 41 in the view shown in FIG. 11. The external thread 42 may make approximately 3½ revolutions around the barrel portion 43, although in other embodiments, the thread 42 may make fewer or more revolutions. The external thread 42 may also taper down near the distal end of the barrel portion 43. This tapering may aid in the fastener's penetration into a subject material, such as a mesh 81. In this embodiment, the thread 42 also tapers at the proximal end of the barrel portion 43, e.g., to having a zero crest height, at or before the head 41, but may instead maintain a relatively constant diameter to a point at which the thread 42 joins the head 41. Having the thread 42 extend to the head 41 may help allow the fastener 4 to be removed from a material, such as mesh 81, by simply rotating the fastener 4 in a reverse direction. On the other hand, such a thread arrangement may permit the fastener 4 to be "overdriven" and pass through a mesh 81 or other material to an undesired depth. Having a gap between the proximal most end of the thread 42 and the head 41 (as shown in FIG. 11) may help stop the fastener insertion at a material surface, and may also cause some materials, such as a mesh 81, to be captured between the thread 42 and the head 41. Other variations to the external thread 42 may be made, such as different thread pitches, a variable thread pitch, different thread face angles (leading and/or trailing faces), thread crest shapes (pointed, flat as shown, rounded, etc.), two or more threads, and so on. The external thread 42 may also have the distal most portion of the thread 42 extend forward of the barrel portion 43, e.g., forming a gimlet, hook or prong portion that may aid in leading the fastener 4 into a material. Also, a pitch of the internal threaded portion of the shaft 2 that engages the pusher element 3 may be the same as, longer, or shorter than a pitch of the external thread 42. In this illustrative embodiment, the thread pitch of the internally threaded portion of the shaft 2 is longer than the thread pitch of the external thread 42, e.g., to help aid in disengaging the fasteners 4 from the mandrel 5 during deployment. In short, any suitable external thread 42 arrangement may be used in some aspects of the invention.

In one aspect of the invention, the barrel portion may have a crenellated front face 431. For example, as shown in FIG. 11, the barrel portion 43 may have a tapered distal end. If the barrel portion 43 has a cylindrical or conical form, the tapered distal end may terminate in a crenellated forward edge 431 in which distalmost portions of the forward edge 431 are received in grooved portions of the mandrel 5 between the splines. This arrangement may aid in penetration of the fastener 4 in a material, e.g., because a leading part of the distal end of the barrel portion 43 first penetrates the material, leading the way for the trailing part of the distal end. It has also been found in some embodiments that the crenellated front face 431 may help cut through material, e.g., in a way similar to a serrated blade. Other arrangements for the distal end of the tack are possible, including a "fish mouth" type feature in which the distal end of the barrel portion 43 has a "V" shaped notch. Alternately, the distal end of the barrel portion 43 may have a sharp leading edge to help penetrate material.

Figure 12:
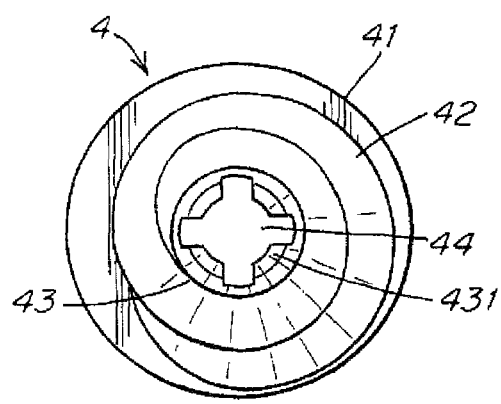
FIG. 12 shows a bottom view of the FIG. 11 fastener.
Figure 13:
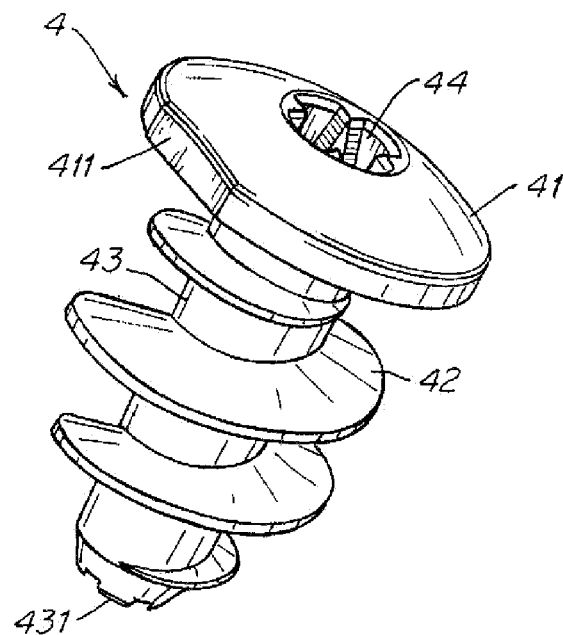
FIG. 13 shows a top perspective view of the FIG. 11 fastener.
Figure 14:
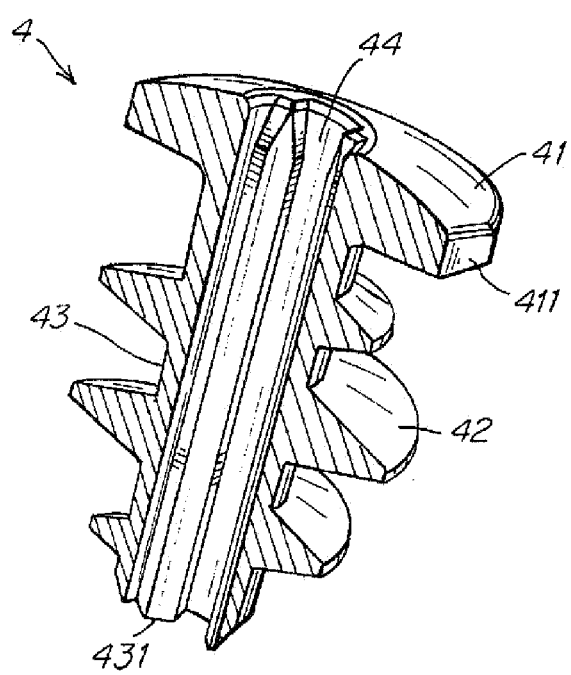
FIG. 14 shows a cross-sectional view of the FIG. 11 fastener.

In another aspect of the invention and as shown in FIGS. 12-14, the fasteners may have a throughbore 44 extending through the barrel portion 43 and the head 41. The throughbore 44 may extend along a longitudinal axis of the barrel portion 43, and provide a pathway through the fastener 4. In one aspect of the invention, the throughbore 44 may have a splined cross section throughout its entire length that mates with the mandrel 5. However, in another embodiment, only a distal portion of the throughbore 44 may include a splined cross section. A proximal portion of the throughbore may have a larger diameter than the distal splined portion, e.g., so that the proximal portion does not engage with the mandrel 5. The proximal portion may have any shape or size, e.g., may have a smooth cylindrically shaped bore. By arranging the throughbore 44 so that only a distal portion of the fastener 4 engages with the mandrel 5, the fastener 4 may be more easily disengaged from the mandrel 5 during deployment. However, it is possible that the throughbore 44 be splined along its entire length, or may be splined only at the proximal end.

As shown in FIGS. 13 and 14, the head 41 of the fastener 4 may include at least one flat side surface 411 or other feature which may help in aligning a plurality of fasteners 4 when mounted on a mandrel 5. Alignment of the fasteners 4 may be important, for example, when the fasteners 4 have a non-symmetrical shape, e.g., include an angled distal face. Of course, an alignment feature may take other forms, such as a bump, notch, groove, hole, marking or other.

The fastener may be made of any suitable biocompatible material, such as an absorbable material (e.g., PLA or other), a non-absorbable metal or plastic (e.g., titanium), or any other material or combination of materials. Further, the fasteners 4 may be made of any suitable size, e.g., about ¼ inch long and about ⅛ inch in diameter with a throughbore diameter of about 1/32 inch.

Figure 15:
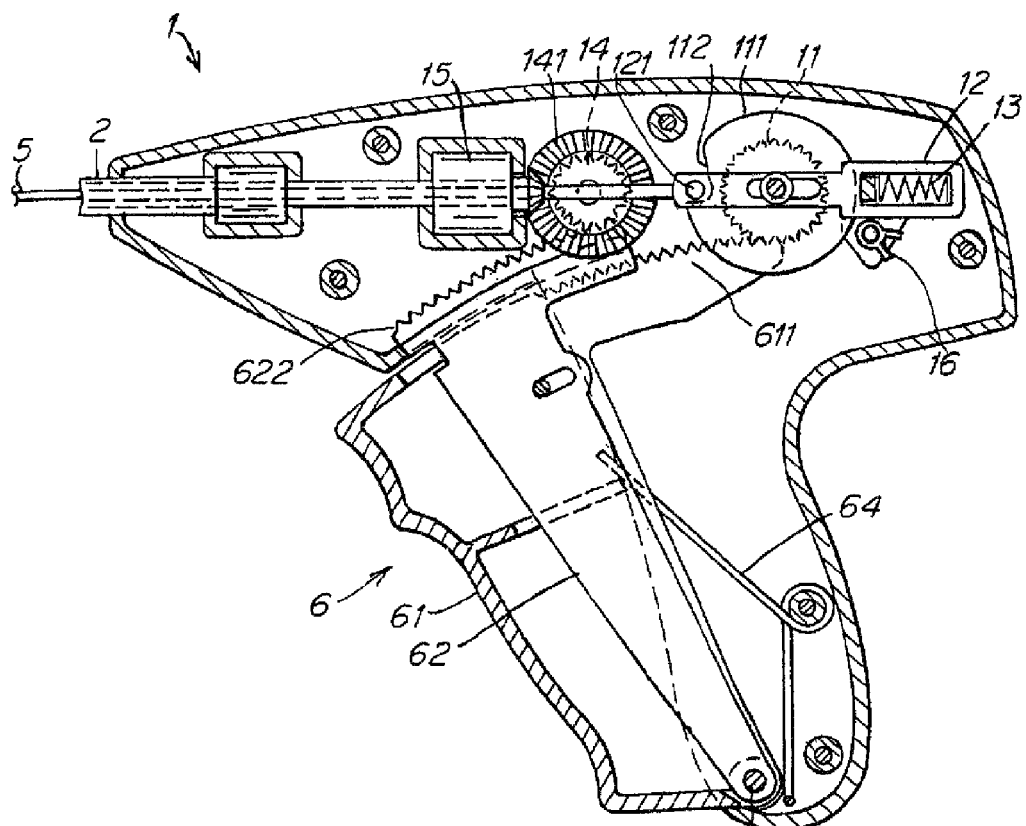
FIG. 15 shows a left-side, cross-sectional view of the handle portion of the fastener applier.
Figure 16:
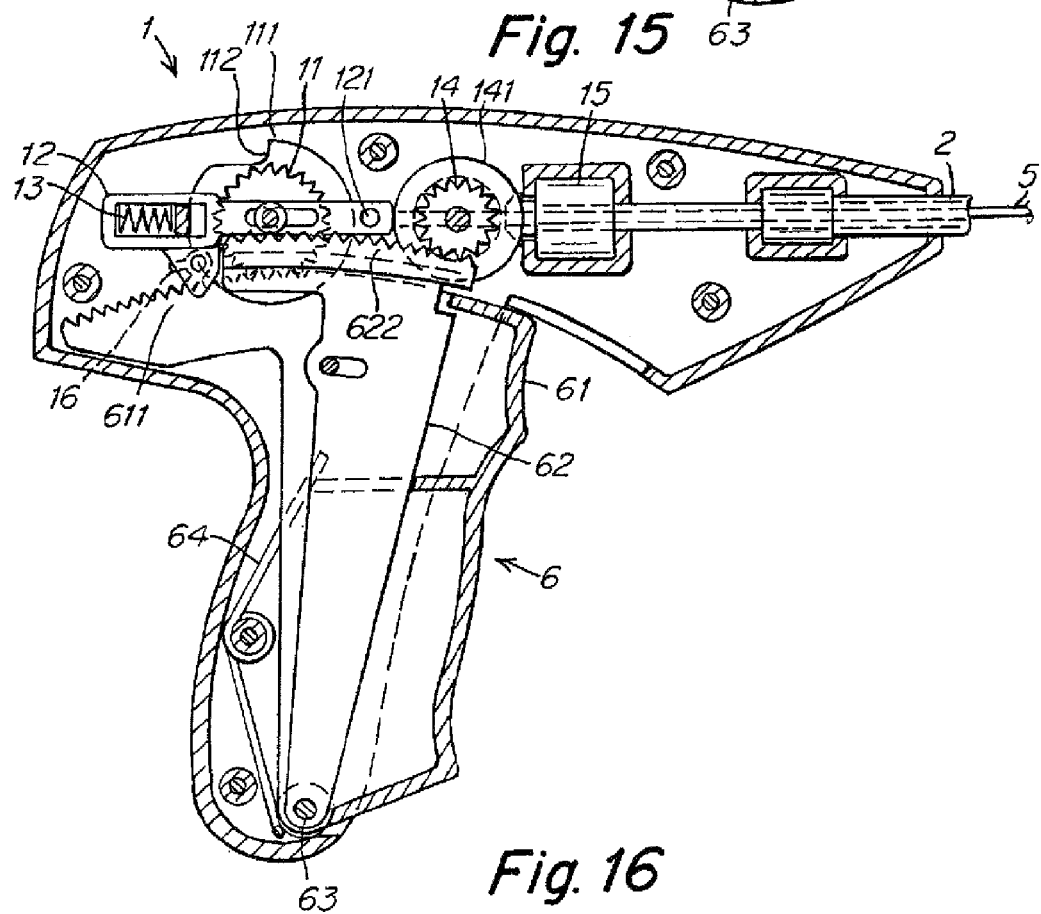
FIG. 16 shows a right-side, cross-sectional view of the handle portion of the fastener applier.

The applier 100 may deploy fasteners 4 using a manually operated mechanism, a motorized mechanism, or a combination of manual and motorized. FIGS. 15 and 16 show left and right side views, respectively, of a manually-operated mechanism for the applier 100 of FIG. 1. In this illustrative embodiment, the handle 1 includes a trigger 6 that has two operable trigger levers 61 and 62 that both pivot about a trigger pivot 63. The outer trigger lever 61 is exposed and is gripped by a user, whereas the inner trigger lever 62 is housed inside of the outer trigger lever 61. Both trigger levers 61 and 62 are urged to a starting position shown in FIG. 15 by a spring 64 or other suitable resilient member. The outer trigger lever 61 includes a mandrel drive rack 611 that has teeth which engage with a mandrel drive pinion 11. Accordingly, as the outer trigger lever 61 is moved toward the handle 1, the mandrel drive rack 611 causes the mandrel drive pinion 11 to rotate (in a counterclockwise direction as shown in FIG. 15). This rotates a mandrel drive cam 111 which is fixed to the pinion 11 and engages with pin 121 on a mandrel slider 12. When the outer trigger lever 61 is in the starting position, a notch 112 in the mandrel drive cam 111 is engaged with the pin 121, allowing the mandrel slider 12 to move proximally (to the right in FIG. 15) under the bias of a spring 13. However, as the outer trigger lever 61 is depressed and the mandrel drive cam 111 rotates, the cam 111 pushes the pin 121 distally, causing the mandrel slider 12 to move distally against the bias of the spring 13. Since the mandrel slider 12 is coupled to the mandrel 5, the mandrel 5 moves distally with the mandrel slider 12. The mandrel slider 12 is only moved distally until the notch 112 is cleared from the pin 121. Thereafter, the mandrel slider 12 and mandrel 5 remain stationary.

During initial movement of the outer trigger lever 61 from the starting position, the inner trigger lever 62 remains stationary. However, upon further depression of the outer trigger lever 61, the outer trigger lever 61 contacts the inner trigger lever 62 so the inner trigger lever 62 rotates about the trigger pivot 63 as well. The inner trigger lever 62 includes a mandrel drive rack 622 that engages with a drive pinion 14 (see FIG. 16). Movement of the inner trigger lever 62 therefore causes rotation of the drive pinion 14 and an associated bevel gear 141, which is engaged with a complementary bevel gear of a clutch 15. As a result, rotation of the drive pinion 14 causes the bevel gear 141 to rotate the clutch 15 (e.g., in a clockwise direction looking from the handle 1 down the shaft 2). The clutch 15 is engaged with the mandrel 5, and thus rotation of the clutch 15 in the clockwise direction causes the mandrel 5 to rotate clockwise as well. Continued depression of the trigger levers 61 and 62 rotates the mandrel 5 and causes a fastener 4 to be deployed as described above. A pawl 16 is arranged to engage with the mandrel drive rack 611 so that once fastener rotation begins (i.e., once the outer trigger 61 contacts the inner trigger 62 and the clutch 15 rotates the mandrel 5), the trigger levers 61 and 62 cannot return to the starting position of FIG. 15 until the trigger levers 61 and 62 are completely depressed. Upon complete depression of the trigger levers 61 and 62, the pawl 16 may clear the mandrel drive rack 611, allowing the mandrel drive rack 611 and trigger levers 61 and 62 to return to the starting position. Return movement of the trigger levers 61 and 62 may cause the mandrel drive pinion 11 and the drive pinion 14 to be backdriven. As a result, the notch 112 returns to engagement with the pin 121, causing the mandrel slide 12 and mandrel 5 to be moved proximally by the spring 13. Although the bevel gear 141 may rotate in reverse during trigger return, the clutch 15 may prevent the mandrel 5 from rotating. Instead, the mandrel 5 remains stationary during trigger return.

Deployment of a distal most fastener 4 may occur during the stroke of the trigger levers 61 and 62, i.e., before the trigger levers 61 and 62 are completely depressed and the pawl 16 clears the mandrel drive rack 611. This arrangement may help ensure that the fastener 4 is disengaged from the mandrel 5 before rotation of the mandrel 5 stops and the mandrel 5 is retracted. For example, the fastener 4 may be arranged to disengage from the mandrel 5 upon three revolutions of the mandrel 5. However, the mandrel 5 may be arranged to rotate 3½ revolutions before stopping. After the mandrel 5 stops rotating, the pawl 16 may be arranged to require further depression of the trigger levers 61 and 62 before the pawl 16 clears the rack 611. During this motion of the trigger levers 61 and 62, other functions may be performed, such as actuating a counter to indicate that a fastener has been deployed. In one embodiment, a display of fasteners deployed and/or fasteners remaining may be provided on the handle 1, e.g., on an LCD or LED display.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A surgical fastener system including:
    a tube having a distal end, a proximal end, and an inner bore;

a plurality of fasteners located in the tube, each of the fasteners having a barrel portion with an external thread and a throughbore extending through the barrel portion, the throughbore having a portion with a non-circular cross-section;

a mandrel located in the inner bore and adapted to pass through the throughbore of each of the plurality of fasteners, the mandrel adapted to engage with the non-circular cross-sectional portion of the plurality of fasteners, the mandrel having a distal end, a proximal end, and a longitudinal axis extending therebetween, the mandrel being arranged for rotation about the longitudinal axis relative to the tube and arranged for movement along the longitudinal axis relative to the tube such that the distal end of the mandrel is extendable from the distal end of the tube, wherein movement of the mandrel along the longitudinal axis does not cause ejection of a distalmost fastener of the plurality of fasteners from the tube; and a handle attached to the proximal end of the tube, the handle including an actuator adapted to cause the distal end of the mandrel to move and extend from the distal end of the tube, the actuator adapted to cause the mandrel to rotate about the longitudinal axis relative to the tube to deploy the distalmost fastener of the plurality of fasteners, the actuator being adapted to retract the distal end of the mandrel into the tube after deployment of the distalmost fastener;

wherein rotation of the mandrel about the longitudinal axis causes rotation of the distalmost fastener engaged with the mandrel and deployment of the distalmost fastener from the distal end of the tube.

2. The system of claim 1, wherein the tube includes a threaded portion of the inner bore.

3. The system of claim 2, further comprising a pusher element adapted to engage with the mandrel for rotation with the mandrel, the pusher including thread elements adapted to engage with the internal threaded portion of the inner bore such that rotation of the pusher element with the mandrel causes the pusher element to move in a direction along the longitudinal axis and to move the plurality of fasteners along the longitudinal axis.

4. The system of claim 3, wherein the plurality of fasteners are arranged to move freely along the mandrel in the direction of the longitudinal axis.

5. The system of claim 3, wherein movement of the pusher element along the mandrel in the direction of the longitudinal axis urges the distalmost fastener on the mandrel to be disengaged from a distal end of the mandrel.

6. The system of claim 1, wherein the mandrel has a sharpened distal end or a gimlet at the distal end.

7. The system of claim 1, wherein the mandrel has a cruciform shape in a cross-section perpendicular to the longitudinal axis.

8. The system of claim 7, wherein the non-circular cross section for each of the fasteners is a cruciform shape complementary to the cruciform shape cross section of the mandrel.

9. The system of claim 1, wherein none of the fasteners located proximally of the distalmost fastener contacts the inner bore of the tube so as to resist axial or rotational movement of the fasteners relative to the tube.

10. The system of claim 1, wherein the actuator includes a manually operated trigger.

11. The system of claim 1, wherein each of the fasteners includes a head portion at a proximal end of the barrel portion, the head portion having a size in a direction transverse to the throughbore that is larger than a size of the barrel portion.

12. The system of claim 1, wherein none of the fasteners located proximally of the distalmost fastener contacts the inner bore of the tube so as to resist axial or rotational movement of the fasteners relative to the tube.

13. A surgical fastener system including:

a tube having a distal end, a proximal end, an inner bore with an internal threaded portion, and a non-threaded restriction element at the distal end;

a plurality of fasteners located in the tube, each of the fasteners having a barrel portion with an external thread and a throughbore extending through the barrel portion, the throughbore having a portion with a non-circular cross-section;

a mandrel located in the inner bore and adapted to pass through the throughbore of the plurality of fasteners, the mandrel adapted to engage with the non-circular cross-sectional portion of at least one of the plurality of fasteners, the mandrel having a distal end, a proximal end, and a longitudinal axis extending therebetween, the mandrel being arranged for rotation about the longitudinal axis relative to the tube; and a pusher element adapted to engage with the mandrel for rotation with the mandrel, the pusher element including thread elements adapted to engage with the internal threaded portion of the inner bore, wherein rotation of the mandrel relative to the tube causes the pusher element to move in a direction along the longitudinal axis and to move the plurality of fasteners along the longitudinal axis relative to the tube;

wherein only rotation of the mandrel about the longitudinal axis, and not movement of the mandrel along the longitudinal axis relative to the tube, causes rotation of a distalmost fastener of the plurality of fasteners engaged with the mandrel and deployment of the distalmost fastener from the distal end of the tube, and wherein prior to deployment, the distalmost fastener is positioned to engage with the non-threaded restriction element to resist axial movement of the distalmost fastener relative to the tube, and wherein prior to deployment of the distal most fastener from the distal end of the tube, none of the fasteners proximal of the distalmost fastener engages with the restriction element or the inner bore of the tube so as to resist axial or rotational movement of the fasteners relative to the tube.

14. A surgical fastener system including:

a tube having a distal end, a proximal end, and an inner bore with an internal threaded portion;

a plurality of fasteners located in the tube, each of the fasteners having a barrel portion with an external thread and a throughbore extending through the barrel portion, the throughbore having a portion with a non-circular cross-section;

a mandrel located in the inner bore and adapted to pass through the throughbore of the plurality of fasteners, the mandrel adapted to engage with the non-circular cross-sectional portion of at least one of the plurality of fasteners, the mandrel having a distal end, a proximal end, and a longitudinal axis therebetween, the mandrel being arranged for rotation about the longitudinal axis relative to the tube; and a pusher element adapted to engage with the mandrel for rotation with the mandrel, the pusher including thread elements adapted to engage with the internal threaded portion of the inner bore;

wherein rotation of the mandrel about the longitudinal axis relative to the tube causes rotation of at least one of the plurality of fasteners engaged with the mandrel and rotation of the pusher element relative to the internal threaded portion, wherein rotation of the pusher element and engagement of the thread elements with the internal threaded portion causes the pusher element to move along the direction of the longitudinal axis in the inner bore, and wherein none of the fasteners located proximally of a distalmost fastener of the plurality of fasteners contacts the inner bore of the tube so as to resist axial or rotational movement of the fasteners relative to the tube.

15. The system of claim 14, wherein the plurality of fasteners are arranged to move freely along the mandrel in the direction of the longitudinal axis.

16. The system of claim 14, wherein the pusher element is arranged to move freely along the mandrel in the direction of the longitudinal axis.

17. The system of claim 14, wherein movement of the pusher element along the mandrel in the direction of the longitudinal axis urges a distalmost fastener on the mandrel to be disengaged from a distal end of the mandrel.

18. The system of claim 14, wherein the mandrel has a sharpened distal end or a gimlet at the distal end.

19. The system of claim 14, wherein the mandrel has a cruciform shape in a cross-section perpendicular to the longitudinal axis.

20. The system of claim 19, wherein the non-circular cross section for each of the fasteners is a cruciform shape complementary to the cruciform shape cross section of the mandrel.

21. The system of claim 14, further comprising a handle attached to the proximal end of the tube.

22. The system of claim 21, wherein the handle includes an actuator adapted to cause the mandrel to rotate about the longitudinal axis.

23. The system of claim 22, wherein the actuator includes a manually operated trigger.

24. The system of claim 22, wherein the actuator is adapted to cause the distal end of the mandrel to extend from the distal end of the tube.

25. The system of claim 14, wherein each of the fasteners includes a head portion at a proximal end of the barrel portion, the head portion having a size in a direction transverse to the throughbore that is larger than a size of the barrel portion.

26. A surgical fastener system including:
a tube having a distal end, a proximal end, and an inner bore with an internal threaded portion;
a plurality of fasteners located in the tube, each of the fasteners having a barrel portion with an external thread and a throughbore extending through the barrel portion, the throughbore having a portion with a non-circular cross-section;
a mandrel located in the inner bore and adapted to pass through the throughbore of the plurality of fasteners, the mandrel adapted to engage with the non-circular cross-sectional portion of at least one of the plurality of fasteners, the mandrel having a distal end, a proximal end, and a longitudinal axis therebetween, the mandrel being arranged for rotation about the longitudinal axis relative to the tube;
a handle attached to the proximal end of the tube, the handle including an actuator adapted to cause the mandrel to rotate about the longitudinal axis and to cause the distal end of the mandrel to move and extend from the distal end of the tube; and
a pusher element adapted to engage with the mandrel for rotation with the mandrel relative to the tube, the pusher element including thread elements adapted to engage with the internal threaded portion of the inner bore;
wherein rotation of the mandrel about the longitudinal axis causes rotation of the at least one of the plurality of fasteners engaged with the mandrel and rotation of the pusher element relative to the internal threaded portion, and wherein rotation of the pusher element and engagement of the thread elements with the internal threaded portion causes the pusher element to move along the direction of the longitudinal axis in the inner bore and to move the plurality of fasteners relative to the tube.

* * * * *